United States Patent [19]
Meyers

[11] 3,951,098
[45] Apr. 20, 1976

[54] HOUSE PLANT WATER CONTENT INDICATOR

[75] Inventor: Edward F. Meyers, Stony Brook, N.Y.

[73] Assignee: Enviro-Gro, Inc., Smithtown, N.Y.

[22] Filed: Feb. 12, 1975

[21] Appl. No.: 549,314

[52] U.S. Cl. .............................. 116/114 AM; 73/73
[51] Int. Cl.² ......................................... G01N 25/56
[58] Field of Search ................ 116/118 A, 114 AM; 73/73, 335

[56] References Cited
UNITED STATES PATENTS

| | | | |
|---|---|---|---|
| 3,019,638 | 2/1962 | Klein | 73/73 |
| 3,824,844 | 7/1974 | Strickland | 73/73 |

*Primary Examiner*—S. Clement Swisher
*Assistant Examiner*—Denis E. Corr
*Attorney, Agent, or Firm*—Mandeville and Schweitzer

[57] ABSTRACT

An indicator device is provided for insertion into the potting soil of a conventional house plant, for monitoring the moisture content thereof. The indicator includes a plastic housing encapsulating an elongated wick extending from a lower point where it is exposed beneath the soil level thereof to an upper point in an indicator chamber formed in the housing. The wick surrounds but does not touch a "signal element" comprising a layer of moisture-sensitive, color changeable substance (e.g., cobalt chloride), to carry moisture to the vicinity of the "signal element". The substance changes color in response to predetermined gains (or losses) in moisture content. Included in the housing structure are a plurality of vents adjacent the indicator chamber for precisely regulating the rate of evaporation therein, to control the response of the indicator to the moisture changes in the soil being monitored. The housing is advantageously comprised of opposed peripherally sealed moisture impervious walls, preferably both transparent, which generally enclose the wick and color change substance and define the overall shape of the indicator device.

8 Claims, 3 Drawing Figures

HOUSE PLANT WATER CONTENT INDICATOR

BACKGROUND AND STATEMENT OF THE INVENTION

Many instruments have been developed in the past which are useful for monitoring moisture content of soil or other life-supporting compositions for growing house plants in pots, window boxes, planters, and the like. However, these instruments have proved unsatisfactory, usually for a variety of reasons. Some are so complicated and contain so many parts that the manufacture thereof makes the final cost prohibitive for amateur gardeners. Other known devices are useful initially and are simple enough in construction to make the cost low enough to make them available for amateurs, however the moisture absorption systems therein tend to become clogged, often because the capillary action thereof carries small particles of soil through the moisture paths contaminating the same, or because the moisture paths are improperly exposed to the ambient atmosphere causing the moist-dry cycle to be disturbed to the extent of providing false indications of moisture content resulting in improper watering of the plant.

With the indicator of the present invention, by contrast, an extremely simple, highly reliable, most economical, and attractive moisture monitoring instrumentality is provided. The new indicator utilizes simply formed and inexpensive materials and is so devised and configured that a proper moisture-dry cycle is established to maintain proper moisture content in the plant soil being monitored. This is achieved by providing a generally elongated housing structure formed of two opposed walls which are comprised, preferably, of a thermoplastic resin so that the opposed walls may be easily heat sealed around the periphery thereof to form a generally elongated flat-like container. Preferably, both walls will be transparent, although it is within the purview of this invention that only the front wall need be transparent.

In accordance with the invention, contained within this generally elongated housing is an elongated wick extending from one end thereof to the opposite end, and being generally of the same shape as the walls of the container. Preferably, the lower end of the housing and the wick contained therein is shaped with a generally pointed configuration, for insertion into the plant soil to be monitored. At this lower end, there is provided a bore through both walls of the housing and the moisture bearing wick, itself, for exposure of the wick to the moisture.

The upper end of the housing is generally larger and somewhat round in configuration, to form a chamber for the signal element. The center of the chamber contains the signal element which is moisture-sensitive substance, e.g., cobalt chloride, which changes color at a predetermined "break point" which is a function of its humidity. Importantly, the moisture indicating substance is surrounded by the wick in the chamber, but is not in actual contact therewith. Moreover, the wick surrounding the moisture signal element has a plurality of spaced bores or openings therethrough in registry with apertures in both walls of the housing.

These openings serve as vents for moisture contained in the chamber. Thus, moisture may be constantly removed from the indicator chamber by evaporation, the rate of which controls the moisture-dry cycle being monitored by the device. The diameter and number of openings in the wick and housing will, of course, affect the rate of evaporation. It is desirable that the upper portion of the housing be configured in the general form of a decorative flower and that the lower portion be shaped as a stem, so that the device, in accordance herewith, is aesthetically pleasing.

Before describing this invention in more detail, it may be well to note that the housing walls of the indicator herein may be fabricated from different thermoplastic resins, including, for example, polyvinyl chloride, polyethylene, polypropylene, "Mylar" (polyethylene terephthalate-Mylar is a Trademark of Du Pont), or similar polyesters. Although it is preferable to utilize a thermoplastic resin because the periphery of the container walls may be readily heat sealed together to form the container, other materials such as metal or glass, or combinations of these with thermoplastic resins may be utilized. Moreover, the wick may be comprised of a conventional felted absorbent material, such as water absorbent blotter material.

Other objects and advantages of this invention will be apparent from the following detailed description, the accompanying drawings, and the appended claims.

DETAILED DESCRIPTION OF THE DRAWINGS

Figure 1:
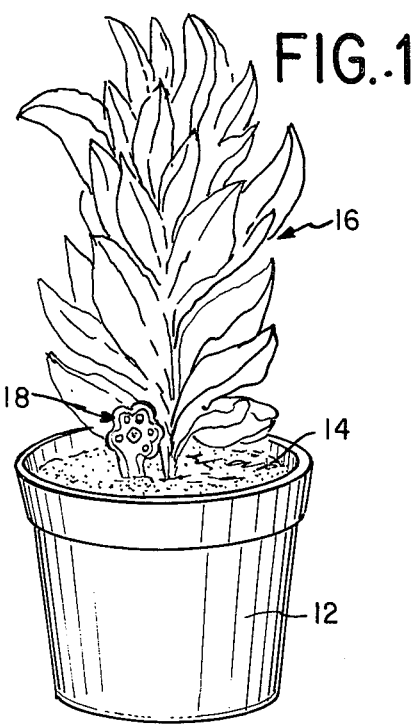
FIG. 1 is a perspective view of a conventional house plant container, with the indicator of the present invention shown in the position in which it is used when placed in the potting soil in the container.

Referring now to the drawings in which like reference characters refer to like elements throughout the several views thereof, a conventional house plant 16 rooted in soil 14 in container 12 is shown in FIG. 1. The moisture monitoring device 18 of the present invention is shown placed in soil 14 for monitoring the moisture content thereof.

Figure 2:
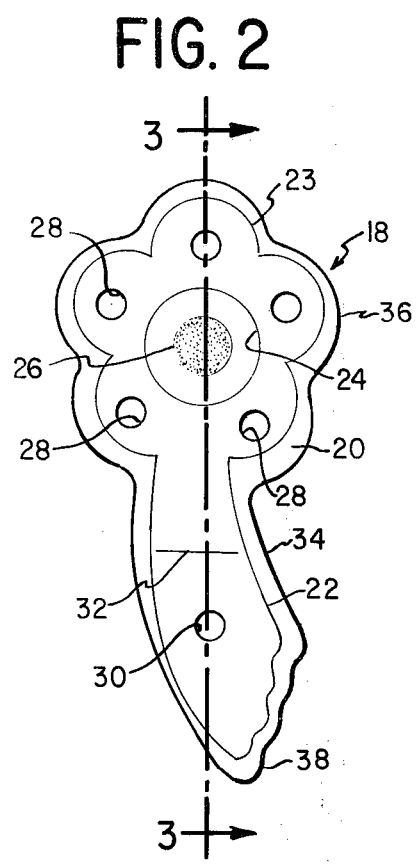
FIG. 2 is a front elevational view of the device of the invention.
Figure 3:
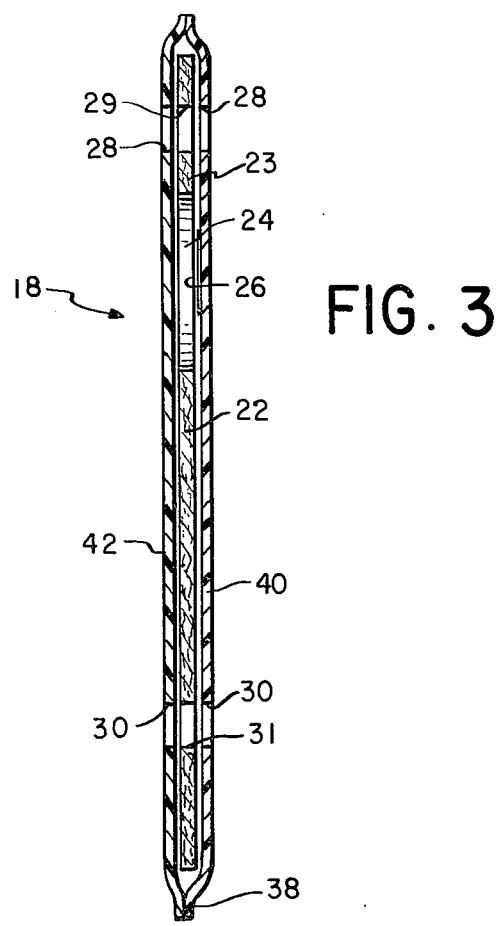
FIG. 3 is a cross-sectional view taken along lines 3—3 of FIG. 2 of the indicator.

Referring now to FIGS. 2 and 3, device 18 of the invention is shown in detail and includes an elongated, generally flat housing 20 having opposed transparent walls 40, 42 heat sealed at the peripheral edges 46 thereof. Disposed in housing 20 is an elongated wick 22, which is shaped generally (although not necessarily) the same shape as housing 20. In the particular embodiment shown, the housing 20 is in the shape of a stylized flower having an upper moisture indicating chamber 36 in the form of a flower body and a lower stem 34 terminating in a pointed portion 38 for insertion into the potting soil or other plant-supporting substance whose moisture is to be measured and monitored. As illustrated in FIG. 2, wick 22 is configured to be in the same general, stylized flower shape as the housing 20. The wick 22 may be comprised of any moisture absorbing material, including fiberglas, a paper blotter-type material or cloth, or other known wicking material, e.g., cellulose sponge.

As best shown in FIG. 3, a bore 30 is formed in the lower stem portion of walls 40, 42, while registering bore 31 is formed in wick 22. The bores 30, 31 provide exposure of the moisture contained in the soil being monitored to the wick 22, for passage of moisture into and upwardly of the wick 22 to the upper flower-shaped portion 23 thereof in the chamber 36. Thus, when the stem portion 34 of the device is inserted into the soil 14, preferably to an indicator line 32, moisture will pass through bores 30, 31 and be absorbed by the wick 22 and conducted into the moisture indicating chamber 36.

The upper portion 23 of wick 22 is generally circular in form, to define petals of a stylized flower which surround central portions of the moisture indicator chamber and forms a sub-chamber 24. Disposed centrally of sub-chamber 24 (in the relation of "pistil and stamens" to the surrounding petals) is the signal element 26, a color-changeable, moisture indicating substance, e.g., cobalt chloride, which may be applied and adhered to the transparent wall 40 of the housing 20. The upper wick portion 23, although surrounding the signal element 26, does not come in actual contact with it. Thus, when moisture passes upwardly through wick 22 into portion 23 thereof, it forms a generally humid condition is sub-chamber 24, which moistens the color changeable substance forming the signal element 26. When the element 26 is comprised of cobalt chloride, it is initially mixed into a body-forming material or paste and stenciled on to wall 40 and allowed to dry. Alternatively, common filter paper may be dipped into a saturated solution of cobalt chloride and allowed to dry and thereafter cut into the size and shape of signal element 26 and adhered to wall 40 within the sub-chamber 24. Preferably, the cobalt chloride will be modified so as to provide a "color break" at a relative humidity level of 75%. Cobalt chloride compositions having color break points at different perdetermined relative humidities are well known to the art and are described, for example, in U.S. Pat. No. 2,627,505, the disclosure of which is incorporated by reference herein.

In accordance with the invention (FIGS. 2 and 3), a plurality of spaced bores or openings 28 are formed in opposed walls 40, 42, surrounding the sub-chamber 24. Moreover, a bore or opening 29 is disposed in the upper portion 23 of the wick 22 in registry with each bore 28. These bores or openings serve as evaporation vents for moisture contained in the upper portion 23 of wick 22, for removing the moisture therein and accommodating the sequential admission or pumping of moisture from the soil being monitored through passage or openings 30, 31 in the lower portion of the device up into the chambers 36, 24.

The cobalt chloride signal element 26 is blue when it is dry and gradually changes hues from blue to reddish blue to pink, and then to pale pink, as the relative humidity in subchamber 24 increases. The sharpness of the "color break" and the R.H. point of the color break is a function of the particular cobalt chloride composition used. Thus, when the soil 14 is watered, moisture will pass through the bores 30, 31 and be absorbed by the wick 22. The moisture passes upwardly in the wick 22 and into the portion 23 thereof surrounding the subchamber 24 and raising the relative humidity therein. The increase in R.H. will be sensed and indicated by a corresponding change in color in the signal element 26. Thereafter, as the moisture evaporates from the soil 14, the wick 22 will gradually dry and because of the vents 28 strategically and regularly spaced around the sub-chamber 24, the moisture will gradually and evenly evaporate from that area, causing the element 26 to change back from light pink to blue, so as to indicate when it is time for rewatering the plant 16. Preferably, as noted above, the stem 34 will be inserted to a depth indicated by a line 32, so that sub-surface moisture is being monitored rather than the surface moisture of soil 14, which, of course, dries quickly and shortly after watering.

Thus, as long as soil 14 is moist, the wick will continually absorb this moisture and evaporate it from the top vents 28. When the soil no longer supplies moisture to the wick, the wick will dry out and the signal element will so indicate by a color change. The size, position and number of evaporating holes may be determined empirically to attain the proper relationship according to the size of housing and the absorption and evaporation characteristics of the wick material being used. For planters or pots containing plants up to about 6 inches in diameter, a wick of paper blotter material and a housing of approximately 4 inches in length and the flower portion of about 1.75 inches wide has proved satisfactory. With an indicator having these parameters, the bores 28 and 30 may be about 0.25 inches in diameter and the bores 29, 31 may be about 0.187 inches in diameter. Larger containers will require larger devices in dimensions scaled in accordance to the size of the container being monitored.

Thus, as will be apparent from the foregoing, moisture monitoring devices are provided, in accordance herewith, which provide for a continuous indication of the moisture content of plant supporting substances, such as potting soil, peat moss, sand and combinations thereof, so that proper moisture content may be maintained therein. Moreover, the devices herein are simple in construction and may be readily produced by mass production techniques, such as stamping operations for stamping out the various simple parts thereof in rapid and large numbers. Moreover, the various individual parts may be joined together by simple heat seal applications to form the device, using relatively inexpensive materials and avoiding the necessity of complicated mechanical arrangements for indicating the moisture content being monitored. Most importantly, despite the elegant simplicity of construction herein, the device of the invention eliminates many of the shortcomings of the prior art devices.

While the form of indicator discussed herein describes and constitutes preferred embodiments of the invention, it is to be understood that the invention is not limited to this precise form of device, and that changes may be made therein without departing from the scope of the invention, which is defined in the appended claims.

I claim:
1. A moisture indicator comprising
   a. an elongated body having two opposed walls joined along the periphery thereof to form a cavity therebetween, the lower end of said body defining means for inserting said body into substances whose moisture content is to be monitored and the upper end thereof defining a moisture indicator chamber, the lower end of said wick having a sample obtaining opening;
   b. wick means disposed in said cavity and extending from the lower end thereof upwardly into said indicator chamber;
   c. the upper end of said wick means having an opening therein defining a sub-chamber within said moisture indicator chamber;
   d. a moisture sensitive, color changeable signal element being adhered to an inner face of one of said opposed walls at a transparent portion thereof and being spaced from said wick means within said sub-chamber;
e. a moisture admission opening formed in said lower end of said housing in registry with said sample obtaining opening in said wick means; and
f. a plurality of registered spaced vent openings formed in upper portions of said wick means and in said opposed housing walls, said vent openings being generally uniformly spaced from and surrounding said sub-chamber.

2. The indicator of claim 1, in which
a. said opposed walls are comprised of a resin selected from the group consisting of polyvinyl chloride, polyethylene, polypropylene, polyethylene terephthalate, and combinations thereof.

3. The indicator of claim 1, in which
said opposed walls are a transparent thermoplastic resin and are heat sealed to one another.

4. The indicator of claim 1, in which
a. said opposed walls are comprised of a material selected from the group consisting of polyvinyl chloride, polyethylene, polypropylene, "Mylar", glass, metal and combinations thereof.

5. The indicator of claim 1, in which
a. said wick means is comprised of a material selected from the group consisting of paper blotter material, fiberglas, fabric, and cellulose sponge.

6. The indicator of claim 1, in which
a. said signal element includes cobalt chloride.

7. The indicator of claim 6, in which
a. said cobalt chloride containing substance has a "color break" responsive to a relative humidity of 75%.

8. The indicator of claim 1, in which
said opposed walls are comprised of glass or metal.

* * * * *